(12) United States Patent
Sawaguchi et al.

(10) Patent No.: US 10,278,898 B2
(45) Date of Patent: May 7, 2019

(54) METHODS FOR MANUFACTURING ENCAPSULATED GRANULAR MATERIAL, METHODS FOR DRYING COATING MATERIALS, AND FLUIDIZED BED DRYERS

(71) Applicant: R.P. Scherer Technologies, LLC, Las Vegas, NV (US)

(72) Inventors: Naoji Sawaguchi, Kakegawa (JP); Yuji Amano, Kakegawa (JP); Yuichiro Sakurai, Kakegawa (JP)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 348 days.

(21) Appl. No.: 15/320,806

(22) PCT Filed: Jun. 26, 2014

(86) PCT No.: PCT/US2014/044319
§ 371 (c)(1),
(2) Date: Dec. 21, 2016

(87) PCT Pub. No.: WO2015/199696
PCT Pub. Date: Dec. 30, 2015

(65) Prior Publication Data
US 2017/0151130 A1    Jun. 1, 2017

(51) Int. Cl.
*A61J 3/07*        (2006.01)
*A61K 9/48*        (2006.01)
(Continued)

(52) U.S. Cl.
CPC ............... *A61J 3/07* (2013.01); *A61J 3/005* (2013.01); *A61K 9/4833* (2013.01);
(Continued)

(58) Field of Classification Search
None
See application file for complete search history.

(56) References Cited

U.S. PATENT DOCUMENTS

| | | | |
|---|---|---|---|
| 4,051,075 A | | 9/1977 | Smith-Johannsen et al. |
| 5,385,737 A | * | 1/1995 | Shigeno .................. A61K 8/11 |
| | | | 264/4.3 |

(Continued)

OTHER PUBLICATIONS

Räsänen, E., "Development of a Novel Multichamber Microscale Fluid Bed with In-line Near Infrared Spectroscopy and Non-invasive Electrostatic Measurement," University of Helsinki, 2003, 52 pages.

(Continued)

*Primary Examiner* — Mary Lynn F Theisen
(74) *Attorney, Agent, or Firm* — Mendelsohn Dunleavy, P.C.

(57) ABSTRACT

Disclosed is a method for shortening the drying time for drying an encapsulated material including a coating material containing water without causing deformation of the coating when drying. The method employs a fluidized bed dryer for drying coating materials that contain water and that form a coating when the water evaporates. A first drying step involves floating and fluidizing the encapsulated material and limiting a theorisable evaporating water content ?W so that dimples or deformation do not occur in the coating of the encapsulated granular material while measuring a water content or temperature of gas exhausted from the fluidized bed dryer; and a second drying step, performed after the measure water content is reduced below a prescribed amount or the measured temperature has increased, of blowing in gas to the fluidized bed dryer so that the theorisable evaporating water content ?W rises above that during the first drying step.

20 Claims, 7 Drawing Sheets

(51) Int. Cl.
- *A61K 9/50* (2006.01)
- *A61K 9/51* (2006.01)
- *B01J 8/24* (2006.01)
- *F26B 3/08* (2006.01)
- *B01J 2/00* (2006.01)
- *B01J 13/04* (2006.01)
- *B01J 2/18* (2006.01)
- *B01J 2/16* (2006.01)
- *B01J 2/06* (2006.01)
- *A61J 3/00* (2006.01)

(52) U.S. Cl.
CPC .......... *A61K 9/5089* (2013.01); *A61K 9/5192* (2013.01); *B01J 2/006* (2013.01); *B01J 2/06* (2013.01); *B01J 2/16* (2013.01); *B01J 2/18* (2013.01); *B01J 8/24* (2013.01); *B01J 13/04* (2013.01); *F26B 3/08* (2013.01)

(56) References Cited

U.S. PATENT DOCUMENTS

| | | | |
|---|---|---|---|
| 2006/0233874 A1* | 10/2006 | Suzuki | A61K 9/4816 424/451 |
| 2007/0082045 A1 | 4/2007 | Yamanaka et al. | |
| 2009/0291168 A1 | 11/2009 | Mangos et al. | |
| 2010/0285121 A1 | 11/2010 | Uchiyama et al. | |

OTHER PUBLICATIONS

Stummer, S., et al. "Fluidized-bed drying as a feasible method for dehydration of Enterococcus faecium M74." Journal of Food Engineering 111.1 (2012): 156-165.

International Search Report and Written Opinion; dated Mar. 25, 2015 for PCT Application No. PCT/US2014/044319.

\* cited by examiner

METHODS FOR MANUFACTURING ENCAPSULATED GRANULAR MATERIAL, METHODS FOR DRYING COATING MATERIALS, AND FLUIDIZED BED DRYERS

TECHNICAL FIELD

The present invention relates to methods for manufacturing encapsulated granular material, methods for drying coating materials, and fluidized bed dryers.

BACKGROUND

Seamless capsules in which medicines are encapsulated in capsules without a seam have been used in recent years for medical and pharmaceutical products and the like (for example, refer to Patent Document 1). Such seamless capsules are formed, for example, by encapsulating the contents with a coating material containing water using a falling-drop method utilizing a multiplex nozzle and drying the coating materials. In the falling-drop method, a double nozzle which includes an inner discharge port for discharging contents to fill the inside of capsules and an outer discharge port for coating materials surrounding the inner discharge port is used for example when manufacturing two-layered capsules. By simultaneously dripping the contents and water-soluble coating materials such as gelatin respectively from the inner discharge port and outer discharge port, the coating materials surround the outer boundary of the contents and become spherical due to surface tension. By dripping these droplets into auxiliary gelation agents, cooling oil, or the like, the coating materials can be solidified while surrounding the content, by taking advantage of gelation and/or solidification due to cooling.

Seamless capsules can be formed for example by blow-drying the solidified coating materials using a rotary drum-type through-flow dryer or a fluidized bed dryer (for example, refer to Patent Document 1 Paragraph [0039]).

PRIOR ART DOCUMENTS

Patent Documents

Patent Document 1: Japanese Patent No. 4,051,075

SUMMARY OF THE INVENTION

Problems to be Solved by the Invention

Figure 8:
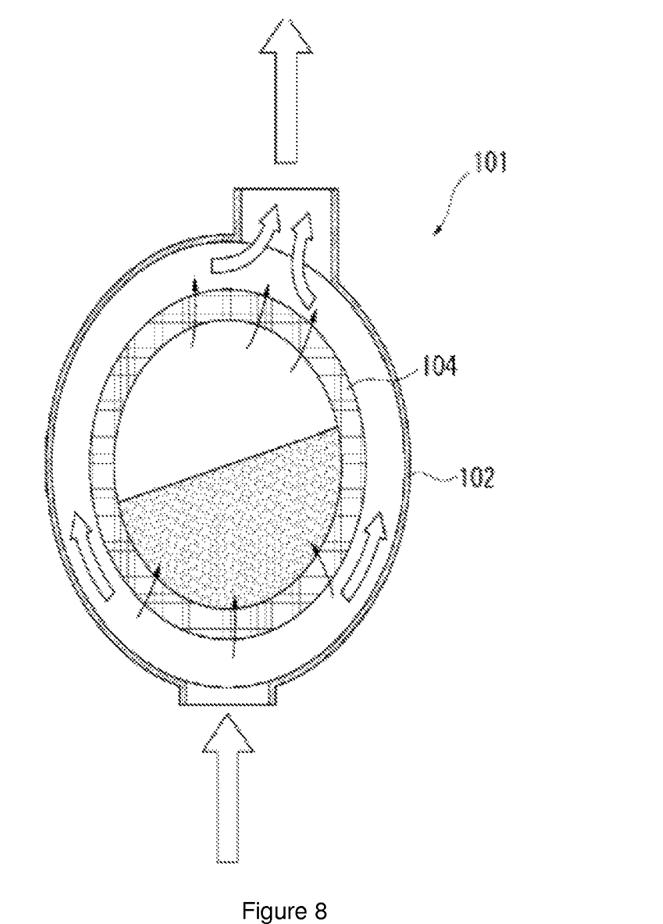
FIG. 8 is a diagram showing a rotary-drum type through-flow dryer.

As indicated with arrows in FIG. 8, part of the supply of drying air passes through between a case 102 and a basket 104 in a rotary drum-type through-flow dryer 101, and the proportion of the drying air that passes through the basket 104 is low. Therefore, the drying efficiency is very low.

In contrast, when a fluidized bed dryer is used, all of the drying air passes through the drying room accommodating the capsules, and therefore the drying efficiency is high. Nevertheless, even when a fluidized bed dryer is used, the drying time is still long, and thus a reduction in the drying time is desired. One possible way to decrease the drying time would be to supply a large amount of drying air of high temperature in a temperature range that would not melt coating materials and would provide low humidity. However, if such drying air of high temperature and low humidity is supplied in a large amount, drying proceeds too rapidly and deformation of the coating of the seamless capsules may occur.

The present invention was made in light of the problems discussed above, and is intended to shorten the drying time for drying seamless capsules without causing deformation of the coating when drying encapsulated granular material that is encapsulated with water-containing coating materials such as gelatin in the form of a seamless capsule and using a fluidized bed dryer.

Means for Solving the Problem

The method for manufacturing the encapsulated granular material of the present invention is directed to a method for manufacturing an encapsulated granular material whose contents are encapsulated with coating. The method comprises a step of creating encapsulated material by encapsulating the contents with a coating material that contains water and forms a coating when the water content of the coating material is decreased. The method comprises a further step of drying the coating material of the encapsulated material by floating and fluidizing the encapsulated material using a fluidized bed dryer. The step of drying the coating materials comprises a first drying step of floating and fluidizing the encapsulated material using a fluidized bed dryer while measuring the water content or temperature of gas exhausted from the dryer after floating and fluidizing the encapsulated material; and a second drying step of blowing gas into the dryer while the operating conditions of the fluidized bed dryer are set so that the theorisable evaporating water content $\Delta W$ rises above that which was present during the first drying step. The second drying step is performed after the measured water content is reduced below a prescribed amount or the measured temperature is increased.

The method for drying coating materials of the present invention is a method for drying coating materials of an encapsulated material whose contents are encapsulated with coating materials that contain water and form a coating when the water content decreases. The drying step is carried out by floating and fluidizing a number of items of encapsulated material using a fluidized bed dryer. The method comprises a first drying step of floating and fluidizing a number of items of encapsulated material while measuring the water content or temperature of gas exhausted after floating and fluidizing the encapsulated material using a fluidized bed dryer. The second drying step comprises blowing gas into the dryer while the operating conditions of the fluidized bed dryer are set so that the theorisable evaporating water content $\Delta W$ rises above that which was presented during the first drying step. The second drying step is performed after the measured water content measured is reduced below a prescribed amount or the measured temperature has increased.

According to the present invention, a shift from a constant-rate drying phase to a decreasing-rate drying phase can be identified by measuring the water content or temperature of gas exhausted after floating and fluidizing the encapsulated material using a fluidized bed dryer. Thereby, the drying time of a decreasing-rate drying phase can be shortened, by controlling a drying air supplying apparatus so that the theorisable evaporating water content $\Delta W$ rises after the measured water content is reduced below a prescribed amount or the measured temperature is increased, i.e., after the shift to a decreasing-rate drying phase. Even if the drying ability of drying air is increased in this manner, deformation of the coating material will not occur because the amount of water evaporating from the coating material is small during the decreasing-rate drying phase.

Preferably, in the method described above, gas blowing by a fluidized bed dryer is controlled during the first drying step so that ΔW/Sa, the ratio of theorisable evaporating water content ΔW of the gas blown in by the fluidized bed dryer to the total surface area Sa of the encapsulated material, is 10 or below.

Preferably, in the method above, gas blowing by a fluidized bed dryer is controlled during the first drying step so that ΔW/Sa, the ratio of theorisable evaporating water content ΔW of the gas blown in by the fluidized bed dryer to the total surface area Sa of the encapsulated material, is 7 or below.

According to the present invention of the configurations described above, coating materials can be dried using drying air with a maximized or maximum drying ability in a manner that will not cause deformation of the capsule coating during a constant-rate drying phase, and, as a result, the coating materials can be dried in a shorter time.

Preferably, in the method above, the theorisable evaporating water content ΔW is calculated based on the product of:
the difference between;
an amount of water vapor per unit weight contained in the gas used for floating and fluidizing the encapsulated material calculated from temperature $t_c$ and the relative humidity $R_c$ of the gas before blowing; and
an amount of saturated water vapor per unit weight that can be contained in the gas exhausted after floating and fluidizing the encapsulated material calculated from the temperature of the exhausted gas, the temperature $t_c$ and the relative humidity $R_c$ of gas before blowing; and
the weight of the gas used for floating and fluidizing the encapsulated material per unit time.

Preferably, in the method described above, the encapsulated granular material is a soft capsule.

Preferably, in the method described above, the encapsulated granular material is a seamless capsule.

Preferably, in the method described above, at least one of the following is performed during the second drying step: raising the temperature of the gas used for floating and fluidizing the encapsulated material to a temperature higher than that used during the first drying step; reducing the humidity of the gas used for floating and fluidizing the encapsulated material to a lower humidity than that used during the first drying step; and increasing the volume of gas used for floating and fluidizing the encapsulated material to a higher volume than the volume used during the first drying step.

The fluidized bed dryer of the present invention is a fluidized bed dryer for drying coating materials of encapsulated material whose contents are encapsulated in coating materials that contain water and form a coating when the water content decreases. The fluidized bed dryer comprises a measuring means or apparatus for measuring a water content or temperature of gas exhausted after floating and fluidizing the encapsulated material using the fluidized bed dryer; and a control means or apparatus, e.g. a controller for controlling at least one of the temperature, humidity and volume of gas blown to the encapsulated material in the fluidized bed dryer based on the water content measured by the measuring means. The control means alters at least one of the temperature, humidity and volume of the gas to be blown when the measured water content is reduced below a prescribed amount or the measured temperature is increased, so that the theorisable evaporating water content ΔW increases when the gas to be blown to the encapsulated material is blown to encapsulated material in the initial drying state.

Preferably, in the fluidized bed dryer described above, the control means controls at least one of the temperature, humidity and volume of the gas blown to the encapsulated material, so that ΔW/Sa, the ratio of the theorisable evaporating water content ΔW of the gas blown in by the fluidized bed dryer to the total surface area Sa of the encapsulated material, is 10 or below, before altering at least one of the temperature, humidity and volume of the gas so that the amount of water evaporation from the coating materials increases.

Preferably, in the fluidized bed dryer described above, the control means controls at least one of the temperature, humidity and volume of the gas blown to the encapsulated material, so that ΔW/Sa, the ratio of the theorisable evaporating water content ΔW of the gas blown in by the fluidized bed dryer to the total surface area Sa of the encapsulated material, is 7 or below, before altering at least one of the temperature, humidity and volume of the gas so that the amount of water evaporation from the coating materials increases.

Preferably, in the fluidized bed dryer described above, the theorisable evaporating water content ΔW is calculated based on the product of:
the difference between;
an amount of water vapor per unit weight contained in the gas used for floating and fluidizing the encapsulated material calculated from the temperature $t_c$ and the relative humidity $R_c$ of the gas before blowing; and
an amount of saturated water vapor per unit weight that can be contained in the gas exhausted after floating and fluidizing the encapsulated material in the fluidized bed dryer calculated from the temperature of the exhausted gas and from the temperature $t_c$ and the relative humidity $R_c$ of the gas before blowing; and
the weight of the gas used for floating and fluidizing the encapsulated material per unit time.

Preferably, in the fluidized bed dryer described above, the encapsulated granular material is a soft capsule.

Preferably, in the fluidized bed dryer method described above, the encapsulated granular material is a seamless capsule.

Effects of the Invention

The drying time using a fluidized bed dryer for drying an encapsulated granular material whose outer boundary is encapsulated with water-soluble substances such as gelatin can be shortened due to the present invention.

MODES FOR CARRYING OUT THE INVENTION

An embodiment of the method for manufacturing encapsulated granular material of the present invention is explained below in detail, while referring to the drawings.

Figure 1:
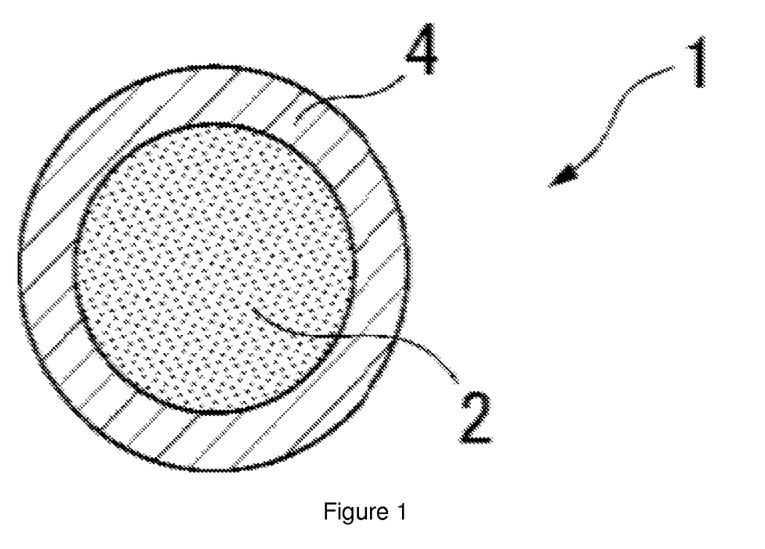
FIG. 1 is a cross-sectional view showing the structure of a seamless capsule manufactured by the manufacturing method of the present embodiment.

FIG. 1 is a cross-sectional view showing the structure of a seamless capsule manufactured by the manufacturing method of the present invention. As shown in the figure, a seamless capsule 1 manufactured by the manufacturing method of the present invention has a two-layer structure formed by a content 2 whose outer boundary is encapsulated with seamless coating 4.

Examples for the content 2 include medical and pharmaceutical products, quasi-drugs, cosmetics, functional foods, health foods, general foods, chemical products, and the like. The contents are not limited to liquids such as lipophilic liquids, hydrophilic liquids, and surfactants, and thus the present invention can be applied even for solids, microcapsules, gels and the like, the present invention can be applied by liquefying the solids, microcapsules, gels and the like by heat-melting or by suspending or dispersing the materials in a liquid or emulsifying them.

Examples for lipophilic liquids include a combination of vitamin E and a medium-chain fatty acid triglyceride in which the vitamin E is dissolved, and the like. Examples of hydrophilic substances include, for example, combinations of ingredients of rhinitis medications, mequitazine, belladonna alkaloid, and anhydrous caffeine, and a medium-chain fatty acid triglyceride oil that functions as a dispersion medium. Hydrophilic substances may also be made suitable for use as the contents 2 by dissolving the hydrophilic substances in one or more polyethylene glycols, which are hydrophilic oily substances. Examples of suitable surfactants include lecithin and the like, and such surfactants may be used as the contents 2 as they are or by dissolving or emulsifying them in oily substances.

Coating 4 is formed by drying a coating material containing water. As used herein, "coating material" refers collectively to the combination of components that forms the precursor material that forms a coating when dried to remove water. For example, gelatinizers such as gelatin, agar, alginate, carrageenan, pectin, and gums such as guar gum, xanthan gum, gum arabic, gellan gum, locust bean gum, tamarind gum, and the like, may be used as coating materials. Coating forming agents such as starch, cellulose, polyvinyl alcohol, and the like that are conventionally used together with the above-mentioned gelatinizers may also be used as part of coating 4.

The gelatinizers may be gelled by use of auxiliary gelation agents such as potassium ions, sodium ions, calcium ions, and ammonium ions.

Such seamless capsules are manufactured as described below.

Figure 2:
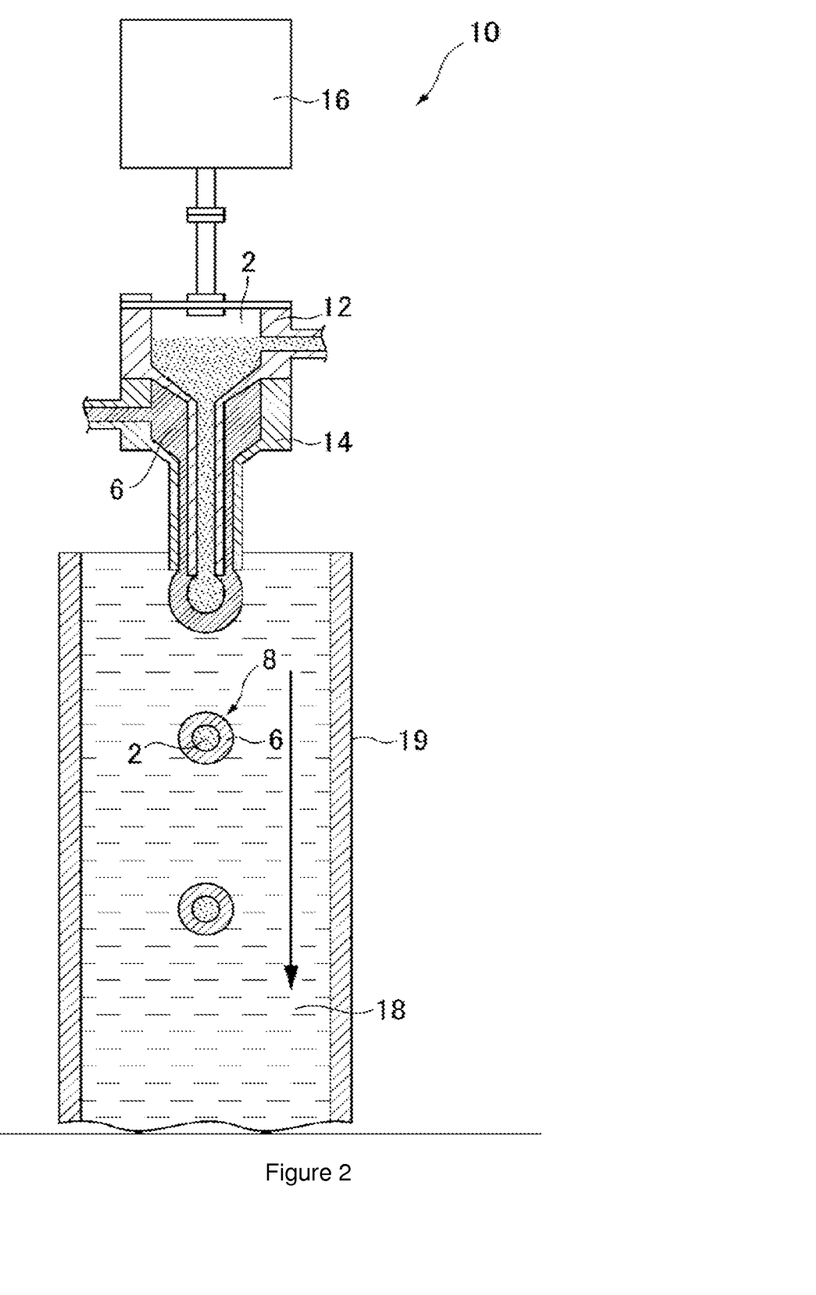
FIG. 2 is a diagram showing a double nozzle for encapsulating contents with coating materials.

FIG. 2 is a diagram showing a double nozzle for encapsulating contents with coating materials. As shown in the figure, a double nozzle 10 comprises an outer nozzle 14 from which a coating material 6 is supplied; an inner nozzle 12 from which contents placed on the inward side of the outer nozzle 14 are supplied; and a vibrator 16 which applies vibrations to the outer nozzle 14 and inner nozzle 12. The tip of the double nozzle 10 is immersed in a container or a liquid flow pipe (in the presently depicted embodiment, a liquid flow pipe) 19 filled with solidifying liquid or cooling oil (referred to below as "solidifying liquid") 18. By applying vibration from the vibrator 16 to the inner nozzle 12 and outer nozzle 14 or pipes, tubes, or the solidifying liquid 18 that are connected to the double nozzle 10 while a content 2 and the coating material 6 are supplied in the inner nozzle 12 and the outer nozzle 14 respectively, the content 2 and the coating material 6 are dripped from the inner nozzle 12 and the outer nozzle 14 respectively. The dripped coating material 6 then surrounds the outer boundary of the content 2 due to the surface tension. Encapsulated material 8 in which the outer boundary of the content 2 is encapsulated in this manner with the coating material 6 is continuously dripped into the liquid flow pipe 19 filled with the solidifying material 18. By being dripped into the solidifying liquid 18, the encapsulated material 8 solidifies while the content is enclosed in the coating material 6. Auxiliary gelation agents such as potassium ions, sodium ions, calcium ions, and ammonium ions may be used as component(s) of such a solidifying liquid.

Figure 3:
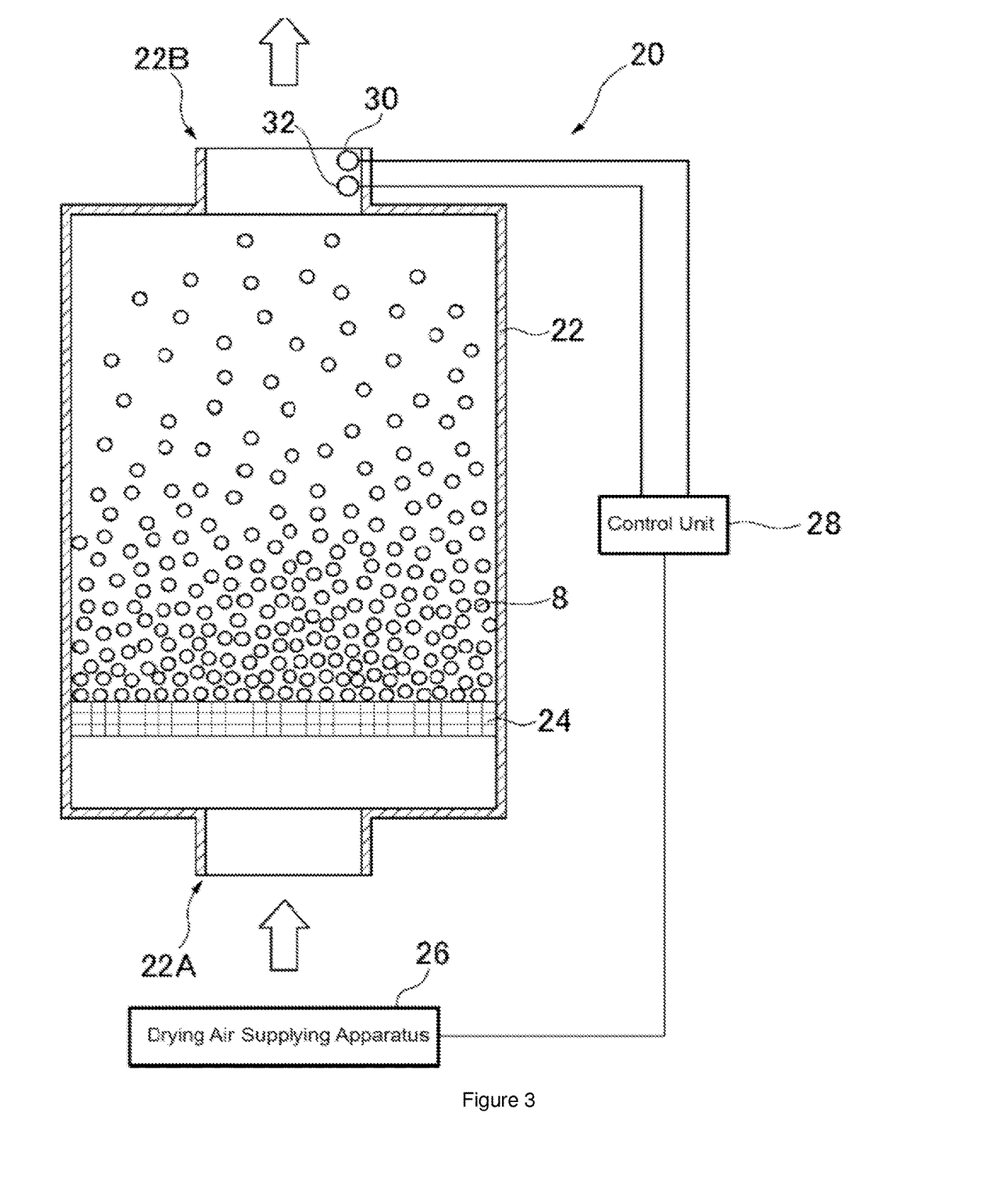
FIG. 3 is a diagram showing the structure of a fluidized bed dryer which may be used in the present invention.

Subsequently, the encapsulated material 8 manufactured in this manner is located in a fluidized bed dryer, and the coating material 6 that surrounds the content 2 is dried. FIG. 3 is a diagram showing the structure of a fluidized bed dryer used in the present embodiment. As shown in the figure, the fluidized bed dryer 20 comprises an exterior case 22 and a straightening board 24 that regulates the flow of drying air placed in the lower part inside the exterior case 22. An inlet 22A into which drying air flows is formed at the bottom of the exterior case 22, and an outlet 22B for exhausting air that has passed through the exterior case 22 (drying room) is formed at the top of exterior case 22.

The fluidized bed dryer 20 further comprises a drying air supplying apparatus 26, a temperature sensor 30 and a humidity sensor 32 attached at the outlet 22B on the exterior case 22, and a control unit 28 that controls the operation of the drying air supplying apparatus 26. The drying air supplying apparatus 26 is connected to the control unit 28, and the temperature, humidity and flow rate of drying air blown from the drying air supplying apparatus 26 to the encapsulated material 8 located in the exterior case 22 may be set through use of the control unit 28.

The drying air supplying apparatus 26 is connected to the inlet 22A of the exterior case 22 and supplies drying air into the exterior case 22. Drying air supplied from the drying air supplying apparatus 26 passes through the inside of the exterior case 22 and is exhausted from the outlet 22B. As a result, the coating material 6 may be dried as the encapsulated material 8 located in the exterior case 22 is floated and fluidized by the drying air.

The temperature sensor 30 and humidity sensor 32, respectively, measure the temperature and humidity of the exhaust air exhausted from the exterior case 22. The temperature sensor 30 and humidity sensor 32 are connected to the control unit 28, and the measured temperature and humidity of the exhaust air are transmitted to the control unit 28.

Here, the present inventors conceived that one of the causes of deformation of coating materials that occurs while drying the coating materials is a reduction in the volume associated with rapid water release from the coating materials. Therefore, the present inventors examined methods for preventing deformation of coatings by preventing rapid water release from the coating materials, as explained below.

First, the inventors conceived that rapid water release from the coating materials may be prevented by altering the temperature, humidity and flow rate of drying air according to the drying time when drying coating materials.

Figure 4:
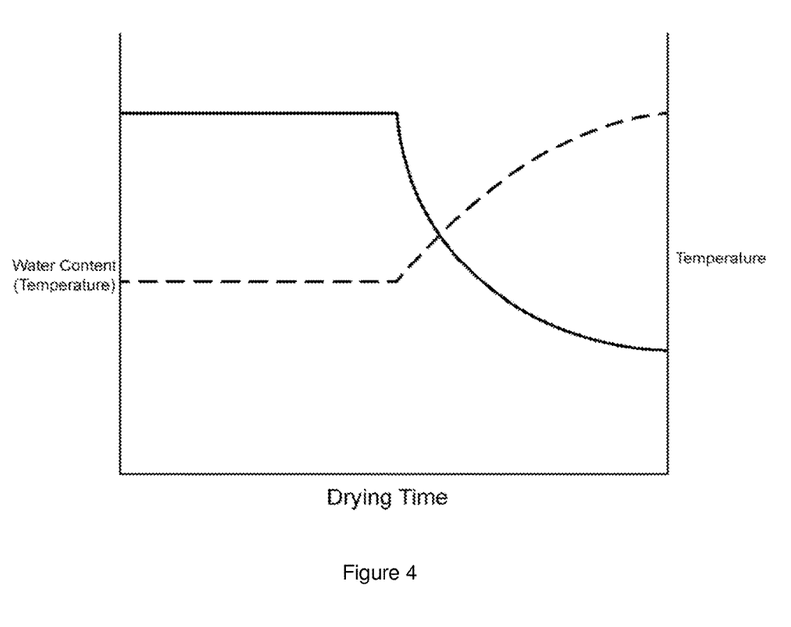
FIG. 4 is a graph showing the water content (relative humidity) and temperature of the exhaust air exhausted when accommodating encapsulated material in the drying room and supplying drying air while keeping the temperature, humidity and air volume constant using the control unit in the fluidized bed dryer of FIG. 3.

FIG. 4 is a graph showing the water content (relative humidity) and temperature of the exhaust air exhausted when the encapsulated material 8 is located in the exterior case 22 and drying air is supplied while keeping the temperature, humidity and volume constant through the control unit 28 in the fluidized bed dryer shown in FIG. 3. As shown in the figure, the humidity of exhaust air (solid line) is roughly 100% until a given time period has passed from when drying started, but the humidity of the exhaust air decreases over time after a certain length of drying time. The temperature of the exhaust air (dashed line) is constant at a low level (wet-bulb temperature) for a given time length from when drying starts but increases over time after the drying time has passed beyond a certain point. The time period from when drying started to when the humidity of exhaust air starts decreasing or the temperature of the exhaust air starts increasing is called the constant-rate drying phase, and the period after the time when the humidity of the exhaust air starts decreasing or the temperature of the exhaust air starts increasing is called the decreasing-rate drying phase.

During the constant-rate drying phase, the amount of water that migrates within the coating materials is large enough so that the equilibration state, in which water keeps evaporating from the coating materials until the humidity of the drying air reaches 100%, continues and the humidity of the exhaust air remains constant. The temperature of the exhaust air will be the wet-bulb temperature, the temperature of the drying air less the temperature component corresponding to the latent heat of evaporation.

In contrast, during the decreasing-rate drying phase, the amount of water that migrates within the coating materials decreases, and therefore the amount of water evaporating from the coating surface decreases, the humidity of the exhaust air decreases, and the temperature and humidity of the exhaust air begin to approach the temperature and humidity of the supplied drying air.

The present inventors originally used to carry out drying with a constant drying ability throughout the constant-rate drying phase and the decreasing-rate drying phase. However, the amount of water evaporating from coating materials per given time during the decreasing-rate drying phase is much smaller than the amount of water evaporating from coating materials per given time during the constant-rate drying phase. In the decreasing-rate drying phase, as the amount of water evaporating from the coating surface is decreasing, most of the water has evaporated, and the volume has shrunk nearly to the volume at the drying end point. Hence, the present inventors conceived that deformation of seamless capsules will not occur even if the drying ability of the drying air is raised as in the present invention and that the drying time can be shortened by raising the drying ability of drying air during the decreasing-rate drying phase to a drying ability that is higher than the drying ability of the drying air during the constant-rate drying phase.

Accordingly, using the ratio of the theorisable evaporating water content per unit time ΔW of drying air to the total surface area Sa of the capsules as an index indicating the amount of water evaporating from the coating materials per unit time, the inventors adjusted the temperature, humidity, and volume of the drying air so that the ratio of the theorisable evaporating water content per unit time ΔW of drying air to the total surface area Sa of the capsules during the constant-rate drying phase is kept at a fixed value or below and the ratio of the theorisable evaporating water content per unit time ΔW of drying air to the total surface area Sa of the capsules during the decreasing-rate drying phase is larger than the ratio of the theorisable evaporating water content per unit time ΔW of drying air to the total surface area Sa of capsules during the constant-rate drying phase.

The inventors decided to divide (theorisable evaporating water content per unit time ΔW of drying air) by (total surface area Sa of capsules), considering that the drying speed of the coating of each capsule has a higher degree of correlation with the surface area of a capsule, which is the evaporation surface, than with the capsule weight (the total water amount to be vaporized). Here, the total surface area Sa of the capsules is the total surface area in the initial drying state, since the number of capsules in both the constant-rate drying phase and the decreasing-rate drying phase does not change and can be considered constant.

The theorisable evaporating water content ΔW herein is the maximum amount of water that can be contained in drying air per unit time, which can be calculated as below.

First, saturated water vapor pressure E at temperature t is calculated using the formula 1 below.

$$E = 6.11 * 10^{(7.5*t/(237.3+t))} \quad \text{Formula 1}$$

Partial water vapor pressure Ep may be calculated using the formula 2 below.

$$Ep = E*RH/100 \quad \text{Formula 2}$$

Specific humidity H (kg/kgDA) may be calculated using the formula 3 below, wherein P (Pa) is atmospheric pressure.

$$H = 18/29 * Ep/(P-Ep) \quad \text{Formula 3}$$

Thus, the specific humidity of the drying air $H_0$ may be calculated using the formula 4 below, wherein the temperature and relative humidity of drying air are $t_c$ (° C.) and $R_c$ (%), respectively, and the atmospheric pressure is 1013.25 Pa.

$$H_0 = 18/29 * 6.11 * 10^{(7.5*tc/(237.3+tc))} * R_c/100/(1013.25 - 6.11 * 10^{(7.5*tc/(237.3+tc))} * Rc/100) \quad \text{Formula 4}$$

Figure 5:
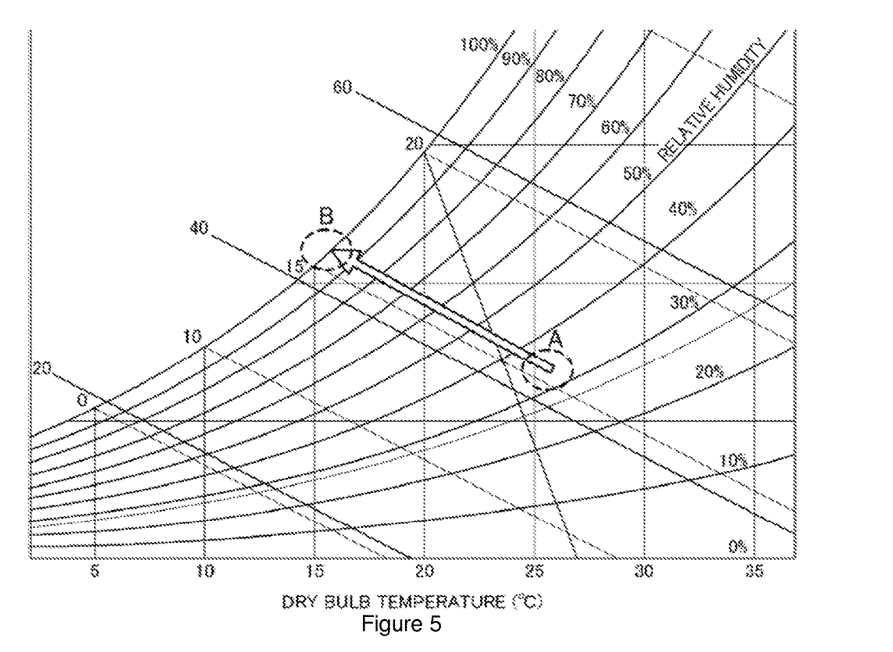
FIG. 5 shows a psychrometric chart.

Air is able to contain water until the relative humidity is 100%. Therefore, the maximum value of the relative humidity of the exhaust air is 100%. The temperature of the drying air decreases due to latent heat as the humidity increases. $T_w$, the temperature of such exhaust air whose relative humidity is 100%, may be calculated, for example, by using the psychrometric chart in FIG. 5 or an approximate expression based on a psychrometric chart. For example, if drying air having a temperature of 26° C. and a relative humidity of 35% RH (Point A in FIG. 5) incorporates water vapor until the relative humidity reaches 100%, the temperature of the exhaust air (Point B in FIG. 5) will be 16° C. Alternatively, the temperature of the exhaust air may be calculated based on latent heat which may be calculated based on the water content of drying air.

Specific humidity of saturated exhaust air $H_W$ may be calculated using the formula 5 below.

$$Hw = 18/29 * 6.11 * 10^{(7.5*tw/(237.3+tw))} * 100/100/(1013.25 - 6.11 * 10^{(7.5*tw/(237.3+tw))} * 100/100) \quad \text{Formula 5}$$

The weight of drying air as dry air G0 may be calculated as in the formula 6 below, using the volume Vc and the humid volume Vh of drying air at a temperature Tc ° C. and a relative humidity Rc %:

$$G0 = Vc/Vh = Vc/(22.4 \times (1/29 + Hc/18) \times (273 + Tc)/273) \quad \text{Formula 6}$$

Thus, the amount of water that can be contained in drying air per minute when the flow rate of drying air is V (m³/min), i.e., the theorisable evaporating water content per unit time ΔW, is the difference between the amount of water vapor per unit volume of the gas used for floating and fluidizing the encapsulated material before blowing and the amount of saturated water vapor that can be contained per unit volume of gas exhausted after floating and fluidizing the encapsulated material, which is calculated by the formula 7 below.

$$\Delta W = (Hw - H_0) \ast G0 \quad \text{Formula 7}$$

Furthermore, the present inventors conceived that the drying time can also be shortened in the constant-rate drying phase by adjusting the theorisable evaporating water content ΔW, while preventing deformation. Here, the inventors expected that deformation of capsules would occur when ΔW/Sa, the theorisable evaporating water content per unit time per unit area of capsules, is high, and conducted the experiments described below using the theorisable evaporating water content ΔW/Sa as an index.

In these experiments, gelatin with glycerin and sorbitol plasticizers, was used as the coating material, and a medium-chain fatty acid triglyceride was used as the content. Encapsulated material was created by dripping the content encapsulated in gelatin into cooling oil.

In these experiments, seamless capsules were manufactured using a fluidized bed dryer under Conditions 1-12, in which the total surface area Sa of capsules located in a fluidized bed dryer, the temperature $t_c$ of drying air during the constant-rate drying phase and decreasing-rate drying phase, the relative humidity $R_c$ of the drying air, and the flow rate V of the drying air were varied. Table 1 shows the total surface area Sa of capsules, the temperature $t_c$ of the drying air during the constant-rate drying phase and decreasing-rate drying phase, the relative humidity $R_c$ of the drying air, and the flow rate V of the drying air under the Conditions 1-12.

TABLE 1

| | | Condition No.: | | | | | |
|---|---|---|---|---|---|---|---|
| | | 1 | 2 | 3 | 4 | 5 | 6 |
| capsules | total number of capsules N | 15700 | 15700 | 27000 | 40000 | 40000 | 40000 |
| | total weight M (kg) | 0.890 | 0.890 | 1.553 | 2.300 | 2.300 | 2.300 |
| | total surface area Sa (m²) | 1.044 | 1.044 | 1.795 | 2.659 | 2.659 | 2.659 |
| | total water content W (kg) | 0.435 | 0.435 | 0.748 | 1.108 | 1.108 | 1.108 |
| drying air (constant-rate drying phase) | drying air temperature tc (° C.) | 26 | 26 | 26 | 35 | 26 | 26 |
| | drying air relative humidity Rc (% RH) | 8.5 | 35 | 8.5 | 22 | 35 | 35 |
| | specific humidity $H_0$ (kgH2O/kgDA) | 0.0018 | 0.0073 | 0.0018 | 0.0077 | 0.0073 | 0.0073 |
| | exhaust air temperature tw (° C.) | 10.7 | 16 | 10.7 | 19.5 | 16 | 16 |
| | exhaust air saturated water vapor content (kgH2O/kgDA) | 0.008 | 0.011 | 0.008 | 0.014 | 0.011 | 0.011 |
| | air volume V (m³/min) | 3.499 | 3.499 | 2.651 | 2.651 | 4.135 | 3.499 |
| | theorisable evaporating water content ΔW (H2O kg/min) | 0.026 | 0.017 | 0.019 | 0.020 | 0.020 | 0.017 |
| | drying time (hr) | 0.200 | 0.330 | 0.580 | 0.550 | 0.420 | 1.250 |
| | ΔW/Sa (H2O g/(m² · min)) | 24.621 | 15.870 | 10.846 | 7.384 | 7.361 | 6.229 |
| drying air (decreasing-rate drying phase) | drying air temperature tc (° C.) | 26 | 26 | 26 | 35 | 26 | 26 |
| | drying air relative humidity (% RH) | 8.5 | 35 | 8.5 | 22 | 35 | 8.5 |
| | air volume V (m³/min) | 3.499 | 3.499 | 2.651 | 2.651 | 4.135 | 3.499 |
| | drying time (hr) | 2.50 | 4.90 | 3.42 | 2.70 | 4.58 | 4.00 |
| total drying time (hr) | | 2.70 | 5.20 | 4.00 | 3.25 | 5.00 | 5.25 |

| | | Condition No.: | | | | | |
|---|---|---|---|---|---|---|---|
| | | 7 | 8 | 9 | 10 | 11 | 12 |
| capsules | total number of capsules N | 40000 | 40000 | 40000 | 40000 | 40000 | 80000 |
| | total weight M (kg) | 2.300 | 2.300 | 2.300 | 2.300 | 2.300 | 2.300 |
| | total surface area Sa (m²) | 2.659 | 2.659 | 2.659 | 2.659 | 2.659 | 5.318 |
| | total water content W (kg) | 1.108 | 1.108 | 1.108 | 1.108 | 1.108 | 2.216 |

TABLE 1-continued

| | | | | | | | |
|---|---|---|---|---|---|---|---|
| drying air (constant-rate drying phase) | drying air temperature tc (° C.) | 26 | 26 | 26 | 26 | 26 | 26 |
| | drying air relative humidity Rc (% RH) | 35 | 35 | 35 | 35 | 35 | 35 |
| | specific humidity $H_0$ (kgH2O/kgDA) | 0.007 | 0.007 | 0.007 | 0.007 | 0.007 | 0.007 |
| | exhaust air temperature tw (° C.) | 16 | 16 | 16 | 16 | 16 | 16 |
| | exhaust air saturated water vapor content (kgH2O/kgDA) | 0.011 | 0.011 | 0.011 | 0.011 | 0.011 | 0.011 |
| | air volume V (m³/min) | 3.499 | 2.651 | 2.651 | 2.651 | 1.590 | 2.651 |
| | theorisable evaporating water content ΔW (H2O kg/min) | 0.017 | 0.013 | 0.013 | 0.013 | 0.008 | 0.013 |
| | drying time (hr) | 1.330 | 1.200 | 1.160 | 1.000 | 1.670 | 2.170 |
| | ΔW/Sa (H2O g/(m² · min)) | 6.229 | 4.719 | 4.719 | 4.719 | 2.831 | 2.359 |
| drying air (decreasing-rate drying phase) | drying air temperature tc (° C.) | 26 | 26 | 35 | 35 | 26 | 35 |
| | drying air relative humidity (% RH) | 35 | 35 | 22 | 22 | 35 | 22 |
| | air volume V (m³/min) | 3.499 | 2.651 | 2.651 | 2.651 | 1.590 | 2.651 |
| | drying time (hr) | 4.87 | 5.60 | 3.59 | 2.80 | 5.33 | 2.83 |
| total drying time (hr) | | 6.20 | 6.80 | 4.75 | 3.80 | 7.00 | 5.00 |

As shown in Table 1, under Conditions 9, 10, and 12, the temperature of the drying air during the decreasing-rate drying phase is higher than the temperature during the constant-rate drying phase, and the relative humidity of drying air during the decreasing-rate drying phase is lower than the relative humidity during the constant-rate drying phase. Therefore, the theorisable evaporating water content per unit time ΔW of the drying air during the decreasing-rate drying phase when applied to encapsulated material in the initial drying state is higher than ΔW of the drying air during the constant-rate drying phase under Conditions 9, 10, and 12. The theorisable evaporating water content per unit time ΔW/Sa of the drying air during the decreasing-rate drying phase when applied to encapsulated material in the initial drying state under Conditions 9, 10, and 12 was equal to the ΔW/Sa during the constant-rate drying phase under Condition 4, which was 7.3844.

Table 2 shows whether deformation such as dimples occurred on the surface of capsules under Conditions 1-12.

TABLE 2

| | | Condition No.: | | | | | |
|---|---|---|---|---|---|---|---|
| | | 1 | 2 | 3 | 4 | 5 | 6 |
| quality post drying | dimples or deformation | large | large | large | slight | slight | none |
| | out of roundness | — | — | 0.981 | | | |

| | | Condition No.: | | | | | |
|---|---|---|---|---|---|---|---|
| | | 7 | 8 | 9 | 10 | 11 | 12 |
| quality post drying | dimple or deformation | none | none | none | none | none | none |
| | out of roundness | 0.98 | 0.978 | | 0.983 | 0.978 | 0.983 |

Figure 6:
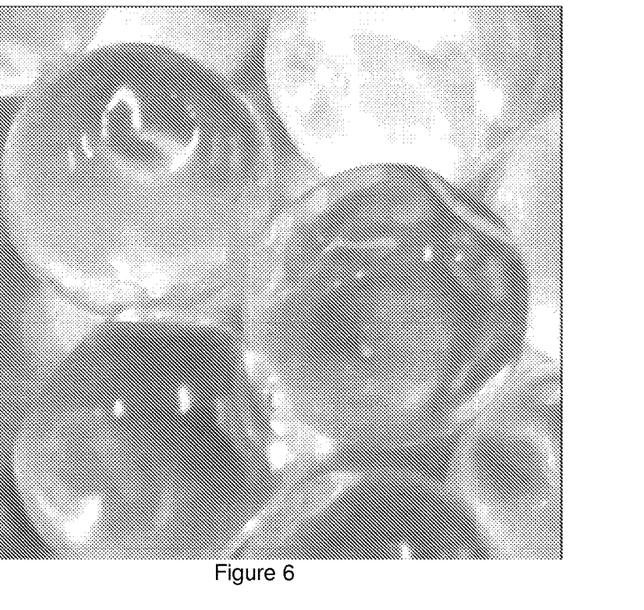
FIG. 6 is a photograph showing seamless capsules post drying of Condition 1.

As shown in Table 2, large dimples or deformations occurred on the surface of seamless capsules under Conditions 1-3. FIG. 6 is a photograph showing seamless capsules post drying under Condition 1. As shown in FIG. 6, deformation occurred and the spherical shape was lost.

Figure 7:
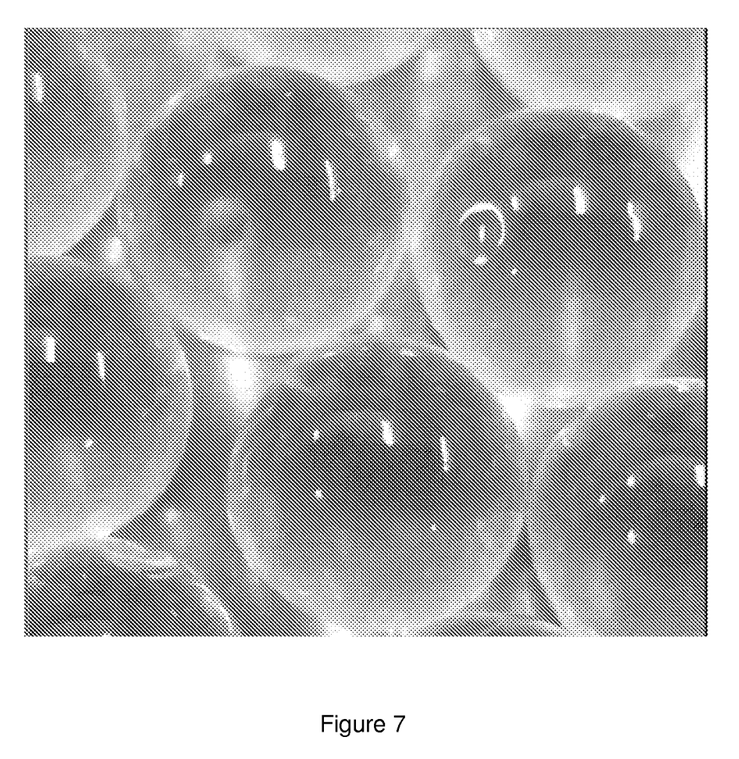
FIG. 7 is a photograph showing seamless capsules post drying of Condition 5.

Under Conditions 4-5, dimples were generated on the surface of seamless capsules. FIG. 7 is a photograph showing seamless capsules post drying of Condition 5. As shown in the figure, slight dimples that would not cause issues when using are generated, while the spherical shape is not lost.

On the other hand, no dimples or deformation occurred on the surface of the seamless capsules made under Conditions 6-12.

According to these results, large dimples or deformations in seamless capsules can be prevented by keeping ΔW/Sa during the constant-rate drying phase at 10 or below, and seamless capsules without any dimples or deformation can be manufactured by keeping ΔW/S a during the constant-rate drying phase at 7 or below.

In Condition 4, the drying ability remained unchanged during the constant-rate drying phase and decreasing-rate drying phase, and the ΔW/Sa for the seamless capsules in the initial drying state was 7.3844. Slight dimples were generated on seamless capsules under Condition 4.

In contrast, under Conditions 9, 10, and 12, the ΔW/Sa for the seamless capsules in the initial drying state was, respectively, 4.7188; 4.7188; and 2.3594 during the constant-rate drying phase, and the ΔW/Sa for the seamless capsules in the initial drying state was changed to 7.3844 during the decreasing-rate drying phase. No deformation or dimples occurred on the surface of the seamless capsules manufactured under Conditions 9, 10, and 12.

According to these results, the drying time of a decreasing-rate drying phase can be shortened and the coating can be dried in a short time as a whole without causing deformation, by increasing the drying ability of drying air during the decreasing-rate drying phase to a drying ability that is higher than the drying ability during the constant-rate drying phase.

Based on the experimental results, the coating material 6 of the encapsulated material 8 is dried in a manner explained below in the present embodiment. Drying is carried out while measuring the temperature and humidity of the exhaust air exhausted from the exterior case 22 using the temperature sensor 30 and the humidity sensor 32.

First, control unit 28 controls the drying air supplying apparatus 26 so that drying air is blown in at a pre-set temperature, relative humidity, and air velocity. Preferably, the temperature, relative humidity, and air velocity of the drying air are set so that $\Delta W/S$ a calculated as above is 10 or below, and more preferably, the temperature, relative humidity, and air velocity of the drying air are set so that $\Delta W/S$ a is 7 or below. The coating material 6 is then dried while floating and fluidizing the encapsulated material by blowing drying air into the exterior case 22, while keeping the temperature, relative humidity, and air velocity constant (the first drying step). This first drying step corresponds to the constant-rate drying phase and the early stage of the decreasing-rate drying phase for the coating material 6.

Second, after detecting that the humidity of the exhaust air measured by the humidity sensor 32 is reduced to or below a prescribed humidity level (for example, 60%), the control unit 28 controls the operating conditions of the drying air supply apparatus 26 so that the drying ability of drying air increases. Specifically, the control unit 28 blows drying air at a temperature, relative humidity, and air velocity that are set so that $\Delta W/S$ a (here, substantially $\Delta W$, since Sa is constant) increases (the second drying step). This drying step corresponds to the middle and later stages of the decreasing-rate drying phase for the coating material 6. Drying air is supplied until the proportion of water in the coating material 6 reaches a set point without altering the temperature, relative humidity and air velocity.

Through the processes above, the coating material 6 is dried and the seamless capsule 1 may be manufactured.

As explained above, once the humidity of the exhaust air measured by the humidity sensor 32 is detected to be reduced to or below a prescribed humidity level, the drying air supplying apparatus 26 is controlled so that the drying ability of drying air increases, i.e., so that the theorisable evaporating water content $\Delta W$ of the drying air when floating and fluidizing the encapsulated material 8 of the initial drying state increases. Thereby, the drying time of the decreasing-rate drying phase can be shortened. Even if the drying ability of the drying air is raised in this manner, deformation of the coating material 6 does not occur because the amount of water evaporating from the coating material 6 is small during a decreasing-rate drying phase.

Furthermore, the control unit 28 controls the drying air supplying apparatus 26 so that $\Delta W/S$ a is preferably 10 or below and more preferably 7 or below during the first drying step (i.e., constant-rate drying phase). Therefore, the coating material 6 can be dried using drying air with the maximum drying ability that will not cause deformation during a constant-rate drying phase, and the coating material 6 can be dried in a shorter time.

In the embodiment above, once the humidity of the exhaust air measured by the humidity sensor 32 was detected to be reduced to or below a prescribed humidity level, the control was carried out so that the drying ability of drying air increases. Alternatively, the control may be carried out so that the drying ability of drying air increases once the temperature of exhaust air measured by the temperature sensor 30 is detected to be raised to or above a prescribed temperature. Similar effects will be provided by such a configuration.

EXPLANATION OF SYMBOLS 1 seamless capsule
2 content
4 coating
6 coating material
8 encapsulated material
10 double nozzle
12 inner nozzle
14 outer nozzle
16 vibrator
18 solidifying material
19 container
20 fluidized bed dryer
22 exterior case
24 straightening board
26 drying air supplying apparatus
28 control unit
30 temperature sensor
32 humidity sensor

The invention claimed is:

1. A method for manufacturing an encapsulated granular material with contents that are encapsulated in a coating, said method comprising steps of:
    creating an encapsulated material by encapsulating the contents with a coating material that contains water and forms a coating when a water content of the coating material decreases; and
    drying said coating material of said encapsulated material by floating and fluidizing said encapsulated material using a fluidized bed dryer;
    wherein said step of drying said coating material comprises:
    a first drying step of floating and fluidizing said encapsulated material while measuring water content or temperature of exhaust gas exhausted after floating and fluidizing said encapsulated material using said fluidized bed dryer; and
    a second drying step of blowing gas into the fluidized bed dryer while operating conditions of said fluidized bed dryer are set so that a theorisable evaporating water content $\Delta W$ rises above the $\Delta W$ during the first drying step; and wherein the second drying step is performed after a measured water content of said exhaust gas is reduced below a prescribed water content or a measured temperature of said exhaust gas is increased.

2. The method for manufacturing the encapsulated granular material of claim 1, wherein gas blown by said fluidized bed dryer is controlled so that $\Delta W/Sa$, the ratio of a theorisable evaporating water content $\Delta W$ of gas blown in by said fluidized bed dryer to a total surface area Sa of said encapsulated material, is 10 or below in the first drying step.

3. The method for manufacturing the encapsulated granular material of claim 1, wherein gas blown by said fluidized bed dryer is controlled so that $\Delta W/Sa$, the ratio of a theorisable evaporating water content $\Delta W$ of gas blown in by said fluidized bed dryer to a total surface area Sa of said encapsulated material, is 7 or below in the first drying step.

4. The method for manufacturing the encapsulated granular material of claim 2, wherein said theorisable evaporating water content $\Delta W$ is calculated based on a product of:

a difference between;
an amount of water vapor per unit weight contained in gas used for floating and fluidizing said encapsulated material calculated from a temperature $t_c$ and a relative humidity $R_c$ of said gas before blowing; and
an amount of saturated water vapor per unit weight that can be contained in gas exhausted after floating and fluidizing said encapsulated material calculated from a temperature of said exhaust gas and from a temperature $t_c$ and a relative humidity $R_c$ of the gas used for floating and fluidizing said encapsulated material before blowing; and
a weight of the gas used for floating and fluidizing said encapsulated material per unit time.

5. The method for manufacturing the encapsulated granular material of claim 1, wherein said encapsulated granular material is a soft capsule.

6. The method for manufacturing the encapsulated granular material of claim 1, wherein said encapsulated granular material is a seamless capsule.

7. The method for manufacturing the encapsulated granular material of claim 1, wherein at least one of the following is performed during the second drying step:
raising a temperature of the gas used for floating and fluidizing said encapsulated material to a temperature higher than a temperature of said gas during the first drying step;
reducing a humidity of the gas used for floating and fluidizing said encapsulated material to a humidity lower than a humidity of said gas during the first drying step; and
increasing a volume of the gas used for floating and fluidizing said encapsulated material to a volume that is higher than a volume of the gas used during the first drying step.

8. A method for drying a coating material that contains water and forms a coating when a water content of the coating material decreases when said coating material is part of an encapsulated material whose contents are encapsulated in said coating material, by floating and fluidizing said encapsulated material using a fluidized bed dryer, said method comprising steps of:
a first drying step of floating and fluidizing said encapsulated material while measuring water content or temperature of exhaust gas after floating and fluidizing said encapsulated material using said fluidized bed dryer; and
a second drying step of blowing gas into the fluidized bed dryer while operating conditions of said fluidized bed dryer are set so that a theorisable evaporating water content $\Delta W$ rises above the $\Delta W$ during the first drying step; and wherein the second drying step is performed after a measured water content of said exhaust gas is reduced below a prescribed amount or a measured temperature of said exhaust gas is increased.

9. The method for drying the coating material of claim 8, wherein gas blown by said fluidized bed dryer is controlled so that $\Delta W/Sa$, the ratio of a theorisable evaporating water content $\Delta W$ of gas blown in by said fluidized bed dryer to a total surface area $Sa$ of said encapsulated material, is 10 or below in the first drying step.

10. The method for drying the coating material of claim 8, wherein gas blown by said fluidized bed dryer is controlled so that $\Delta W/Sa$, the ratio of a theorisable evaporating water content $\Delta W$ of gas blown in by said fluidized bed dryer to a total surface area $Sa$ of said encapsulated material, is 7 or below in the first drying step.

11. The method for drying the coating material of claim 9, wherein said theorisable evaporating water content $\Delta W$ is calculated based on product of:
a difference between;
an amount of water vapor per unit weight contained in gas used for floating and fluidizing said encapsulated material calculated from a temperature $t_c$ and a relative humidity $R_c$ of said gas before blowing; and
an amount of saturated water vapor per unit weight that can be contained in gas exhausted after floating and fluidizing said encapsulated material calculated from a temperature of said exhaust gas and from a temperature $t_c$ and a relative humidity $R_c$ of the gas used for floating and fluidizing said encapsulated material before blowing; and
a weight of the gas used for floating and fluidizing said encapsulated material per unit time.

12. The method for drying the coating material of claim 8, wherein said method forms an encapsulated granular material that is a soft capsule.

13. The method for drying the coating material of claim 8, wherein said method forms an encapsulated granular material that is a seamless capsule.

14. The method for drying the coating material of claim 8, wherein at least one of the following steps is performed during the second drying step:
raising a temperature of the gas used for floating and fluidizing said encapsulated material to a temperature that is higher than a temperature of said gas during the first drying step;
reducing a humidity of the gas used for floating and fluidizing said encapsulated material to a humidity that is lower than a humidity of said gas during the first drying step; and
increasing a volume of the gas used for floating and fluidizing said encapsulated material to a volume that is higher than a volume of said gas during the first drying step.

15. A fluidized bed dryer for drying coating materials that contain water and form a coating on a dried, encapsulated granular material when a water content of said coating materials decreases when said coating material is part of an encapsulated material whose contents are encapsulated in said coating material, said drying being accomplished by blowing gas in the fluidized bed dryer and floating and fluidizing said encapsulated material, said fluidized bed dryer comprising:
a measuring device for measuring water content or temperature of gas exhausted from said fluidized bed dryer after floating and fluidizing said encapsulated material using said fluidized bed dryer; and
a control apparatus for controlling at least one of a temperature, a humidity and a volume of the gas blown to said encapsulated material in the fluidized bed dryer responsive to the water content or the temperature measured by said measuring device,
wherein said control means alters at least one of a temperature, a humidity and a volume of the blown gas when said measured water content is reduced below a prescribed amount or said measured temperature increases, so that a theorisable evaporating water content $\Delta W$ rises above the $\Delta W$ in an initial state of said blown gas.

16. The fluidized bed dryer of claim 15, wherein said control means controls at least one of the temperature, the humidity and the volume of gas blown to said encapsulated material, so that $\Delta W/S\,a$, the ratio of the theorisable evaporating water content ΔW of gas blown in by said fluidized bed dryer to a total surface area Sa of said encapsulated material, is 10 or below, before altering at least one of the temperature, the humidity and the volume of gas so that an amount of water evaporation from said coating material increases.

17. The fluidized bed dryer of claim 15, wherein said control means controls at least one of the temperature, the humidity and the volume of gas blown to said encapsulated material, so that ΔW/Sa, the ratio of the theorisable evaporating water content ΔW of the gas blown in by said fluidized bed dryer to a total surface area Sa of said encapsulated material, is 7 or below, before altering at least one of the temperature, the humidity and the volume of gas so that an amount of water evaporation from said coating material increases.

18. The fluidized bed dryer of claim 16, wherein said theorisable evaporating water content ΔW is calculated based on a product of:

a difference between;
    an amount of water vapor per unit weight contained in gas used for floating and fluidizing said encapsulated material calculated from a temperature $t_c$ and a relative humidity $R_c$ of said gas before blowing; and
    an amount of saturated water vapor per unit weight that can be contained in gas exhausted after floating and fluidizing said encapsulated material calculated from a temperature of said exhaust gas and from a temperature $t_c$ and a relative humidity $R_c$ of the gas used for floating and fluidizing said encapsulated material before blowing; and
a weight of the gas used for floating and fluidizing said encapsulated material per unit time.

19. The fluidized bed dryer of claim 15, wherein said dried, coated encapsulated material forms an encapsulated granular material that is a soft capsule.

20. The fluidized bed dryer of claim 15, wherein said dried, coated encapsulated material forms an encapsulated material that is a seamless capsule.

* * * * *